United States Patent
Mannlein et al.

(10) Patent No.: US 7,704,221 B2
(45) Date of Patent: Apr. 27, 2010

(54) HEATER COOLER VALVE

(75) Inventors: Guy C. Mannlein, Ann Arbor, MI (US);
John M. Adams, Ann Arbor, MI (US);
David Danielson, Chelsea, MI (US);
Brian M. Boniface, Rochester Hills, MI (US)

(73) Assignee: Terumo Cardiovascular Systems, Corporation, Ann Arbor, MI (US)

( * ) Notice: Subject to any disclaimer, the term of this patent is extended or adjusted under 35 U.S.C. 154(b) by 555 days.

(21) Appl. No.: 11/610,558

(22) Filed: Mar. 22, 2007

(65) Prior Publication Data
US 2007/0197951 A1    Aug. 23, 2007

Related U.S. Application Data

(60) Provisional application No. 60/775,111, filed on Feb. 21, 2006.

(51) Int. Cl.
*A61M 37/00*    (2006.01)
*F16K 5/10*    (2006.01)
*F16K 5/00*    (2006.01)

(52) U.S. Cl. .................. 604/6.1; 604/6.13; 604/6.01; 604/6.11; 604/4.01; 251/208; 137/15.22

(58) Field of Classification Search .............. 604/4.01, 604/6.1, 6.11, 6.13; 137/15.21, 111, 339, 137/340, 341; 251/208, 304
See application file for complete search history.

(56) References Cited

U.S. PATENT DOCUMENTS

| | | | | |
|---|---|---|---|---|
| 4,014,382 A | * | 3/1977 | Heath ....................... | 165/60 |
| 5,702,358 A | * | 12/1997 | Witherspoon et al. ........ | 604/6.1 |
| RE36,386 E | * | 11/1999 | Abbott et al. .............. | 604/6.13 |
| 6,389,840 B2 | * | 5/2002 | Feuerecker ................ | 62/434 |

* cited by examiner

*Primary Examiner*—Leslie R Deak
(74) *Attorney, Agent, or Firm*—Gael Diane Tisack, Esq.; MacMillan, Sobanski & Todd, LLC (57) ABSTRACT

A rotary valve unit is provided for blending fluid sources to regulate a temperature of fluid flowing to a heat exchange device in an extracorporeal blood perfusion circuit. A valve body includes a valve chamber having a first inlet port, a second inlet port, a first outlet port, and a second outlet port. A wedged-shaped rotary valve is disposed within the valve chamber and is rotatable within the valve chamber for controlling a blending of the cold fluid entering the fluid chamber from the first inlet port and the return fluid entering the fluid chamber from the second inlet port to regulate the desired temperature of fluid provided to the heat exchanger. The wedge-shaped rotary valve is positionable to provide either only cold fluid to the first outlet port, only return fluid to the first outlet port, or blending of the cold fluid and return fluid to the first outlet port.

19 Claims, 4 Drawing Sheets

HEATER COOLER VALVE

CROSS-REFERENCE TO RELATED APPLICATIONS

This application claims the benefit of U.S. Provisional Application No. 60/775,111 filed Feb. 21, 2006, the disclosure of which is incorporated by reference.

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING COMPACT DISC APPENDIX

Not Applicable

BACKGROUND OF THE INVENTION

1. Field of Invention

The present invention relates in general to cardiac surgery, and, more specifically, to the heating and cooling of blood or other fluids delivered to a patient during cardiac bypass surgery.

2. Background of Related Art

Heating and cooling devices are an important part of blood perfusion systems used during cardiac surgery. During surgery, blood is cooled in a bypass circuit to induce hypothermia to protect the organs. When the surgery has been completed, the blood is re-warmed prior to the patient waking from anesthesia. A "cooler heater" unit device in the bypass circuit is used to cool and heat the cardiac fluid.

A heat transfer fluid such as purified water circulates through a pump in a first circuit and is selectably heated or cooled before being sent to a heat exchange unit. A second circuit carries cardiac fluid to the heat exchange unit. The heat exchange unit includes two chambers. The chambers are separated by a thermally conductive barrier. The warm/cold water (or other heat exchange fluid) in the first circuit is circulated through a first chamber of the heat exchange unit. The cardiac fluid from the patient is circulated through a second chamber of the heat exchange unit. The warm/cold water and the cardiac fluid are each contained in their respective closed circuits, and as a result, are not allowed to mix. The warm or cold water circulated to the first chamber of the heat exchange unit either adds or removes heat as necessary from the cardiac fluid circulated through the second chamber.

The system for providing the temperature controlled water to the heat exchange unit typically includes a cold storage tank, a manifold (i.e., heater and temperature sensing unit), a pump, valves, and water ports. The cold storage tank allows for a volume of water to fill the first circuit, the water side of the heat exchanger, and the portion of the tank contacting the cooling media (e.g., ice). The manifold typically contains a heating element and temperature sensing devices for determining the current temperature of the water flowing to the heat exchange unit. The valves include a set of isolation valves which are actuated between an open or closed position to determine whether water is circulated to the cold storage tank. An electronic controller controls the valve positions and selectably activates a heating device when heating is required. The combined actuation of the valves in cooperation with the heating element regulates the temperature of the water provided to the heat exchange device.

After a temperature setting is input to the controller, the controller measures the temperature of the water flowing to the heat exchange unit and determines whether the temperature needs to be increased, maintained or decreased. If the temperature needs to be increased, then a solenoid valve supplying the cold water from the tank is closed and the heater is turned on. If the temperature needs to be decreased, then the heater is turned off and the solenoid valve to the cold water supply is opened and a portion of the cold water from the tank is supplied to the heat exchange unit. A disadvantage of the above described system is that there are multiple internally piloted solenoid valves which require couplings between fluid conduits and valves which are potential for leaks. In addition, the solenoid valves are continuously actuated and are noisy. Such noise is undesirable during surgery. Moreover, such prior art systems are susceptible to malfunctions due to foreign particulates in the water, and the temperature control of such prior art systems are susceptible to thermal spikes and thermal overshoots.

BRIEF SUMMARY OF THE INVENTION

The present invention advantageously utilizes a rotary valve driven by a motor for supplying cold, warm, or blended cold/warm water for regulating water to a heat exchange unit. The valve provides for a quiet operation and provides for greater temperature control of the water supplied to the heat exchange unit. In addition, the valve is made of plastic for greater resistance to chemicals and less susceptibility to the build of scale and other foreign particulates. In addition, since the rotary valve gradually blends of the return fluid with the cold water supply, a constant flow rate is always maintained to the heat exchange unit and the system is less susceptible to pressure drops.

In one aspect of the present invention, a rotary valve unit is provided for blending hot and cold fluid sources to regulate a temperature of fluid flowing to a heat exchange device in an extracorporeal blood perfusion circuit. A valve body includes a valve chamber having a first inlet port, a second inlet port, a first outlet port, and a second outlet port. A first fluid channel is in fluid communication with the first inlet port. The first fluid channel receives a cold fluid from a cold storage tank. A second fluid channel is in fluid communication with the second inlet port. The second fluid channel receives a returned fluid from the heat exchange device. A third fluid channel is in communication with the first outlet port. The third fluid channel returns fluids received from the inlets to the cold storage tank. A fourth fluid channel is in communication with the second outlet port. The second outlet port returns fluids received from the inlets to the heat exchange device. A wedged-shaped rotary valve is disposed within the valve chamber. The rotary valve is rotatable within the valve chamber for controlling a blending of the cold fluid entering the fluid chamber from the first inlet port and the return fluid entering the fluid chamber from the second inlet port to regulate the desired temperature of fluid provided to the heat exchanger. The wedge-shaped rotary valve is positionable to provide either only the cold fluid to the first outlet port, only the return fluid to the first outlet port, or a blending of the cold fluid and return fluid to the first outlet port.

In yet another aspect of the present invention, an extracorporeal blood perfusion system is provided for controlling the temperature of cardiac fluids during surgery. The system includes a heat exchange unit and a multi-port valve body. A multi-port valve body includes a valve chamber. The valve chamber includes a first inlet port, a second inlet port, a first outlet port, and a second outlet port. A rotary valve is disposed within the valve body. The rotary valve is rotatable within the valve body for fluidically coupling at least two ports of the valve body. A first fluid circuit is coupled to the multi-port valve body for distributing the heat exchange fluid to a heat exchange device. A cold storage tank is coupled to the first fluid circuit between the first inlet port and the first outlet port for cooling the heat exchange fluid. A manifold unit is coupled to the first fluid circuit between the second inlet port and the second outlet port for heating the heat exchange fluid. A pump maintains a fluid flow of heat exchange fluid within the first circuit. A second fluid circuit distributes cardiac fluid to the heat exchange unit. A controller controls the rotation of the rotary valve for regulating the temperature of the heat exchange fluid within the first fluid circuit that is provided to the heat exchange unit. The heat exchange fluid with the first fluid circuit provided to the heat exchange unit regulates the cardiac fluid of the second fluid circuit that that is provided to the heat exchange unit.

In yet another aspect of the present invention, a manifold module is provided for blending hot and cold fluid sources to regulate a temperature of fluid flowing to a heat exchange device in an extracorporeal blood perfusion circuit. A valve body includes a valve chamber having a first inlet port, a second inlet port, a first outlet port, and a second outlet port. A first fluid channel is in fluid communication with the valve chamber and a first inlet port. The first fluid channel receives a cold fluid from a cold storage tank. A second fluid channel is in fluid communication with the valve chamber and the second inlet port. The second fluid channel receives a returned fluid from the heat exchange device. A third fluid channel is in communication with the valve chamber and the first outlet port. The third fluid channel returns fluids received from the inlets to the cold storage tank. A fourth fluid channel is in communication with the valve chamber and the second outlet port. The second outlet port returns fluids received from the inlets to the heat exchange device. A wedged-shaped rotary valve is disposed within the valve chamber. The rotary valve is rotatable within the valve chamber for controlling a blending of the cold fluid entering the fluid chamber from the first inlet port and the return fluid entering the fluid chamber from the second inlet port to regulate the desired temperature of fluid provided to the heat exchanger. The wedge-shaped rotary valve is positionable to provide either only the cold fluid to the first outlet port, only the return fluid to the first outlet port, or a blending of the cold fluid and return fluid to the first outlet port. A heating unit is provided for warming heat exchange fluid exiting the first outlet port. A temperature sensor monitors the temperature of the heat exchange fluid exiting the first outlet port.

Various objects and advantages of this invention will become apparent to those skilled in the art from the following detailed description of the preferred embodiment, when read in light of the accompanying drawings.

DETAILED DESCRIPTION OF THE PREFERRED EMBODIMENT

Figure 1:
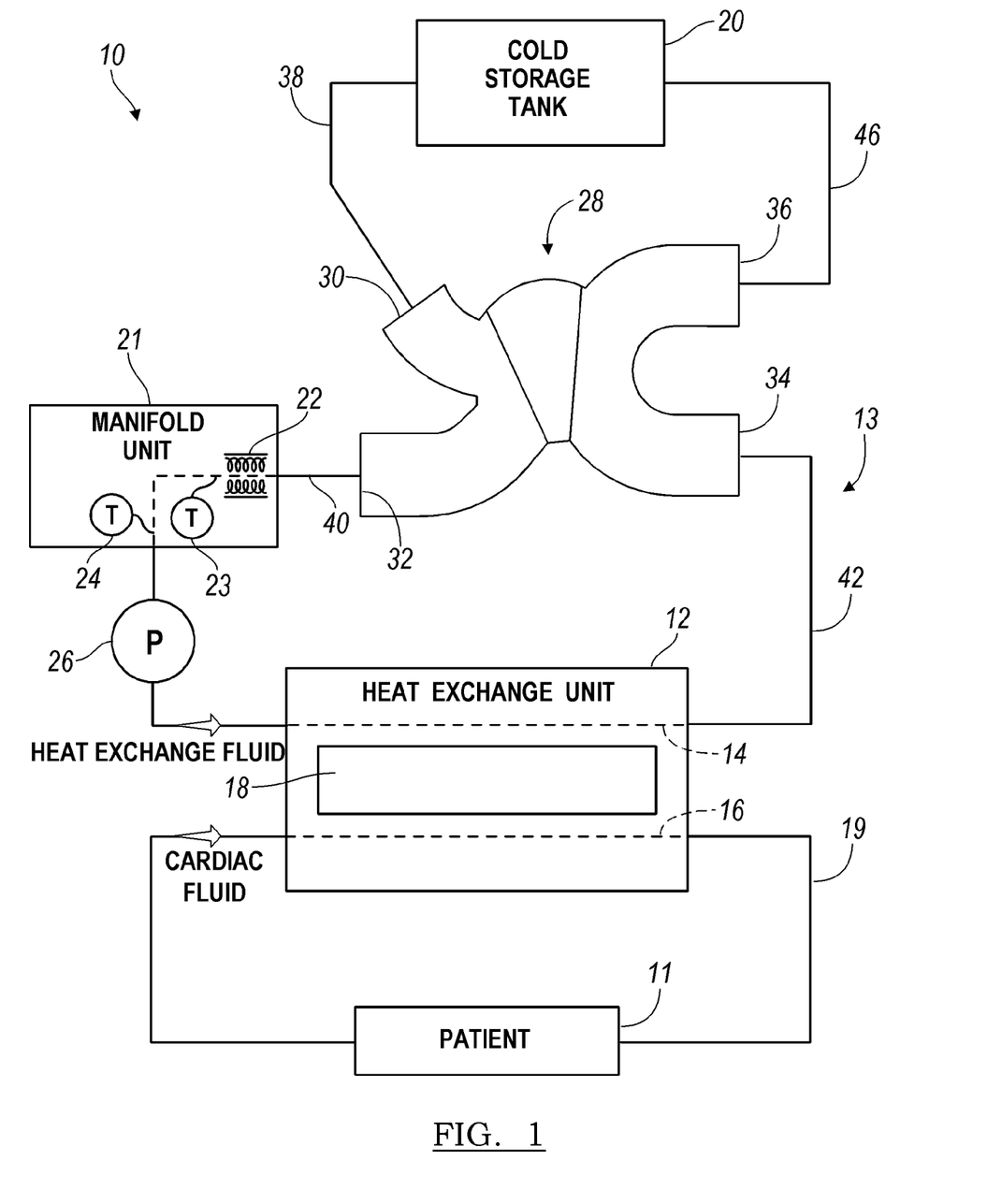
FIG. 1 is a perspective view of a schematic diagram of an extracorporeal blood perfusion system according to a first preferred embodiment of the present invention.

Referring to the Drawings and in particular to FIG. 1, there is shown an extracorporeal blood perfusion system 10 used in the support of cardiac surgery for a patient 11. The system regulates the temperature of the patient's cardiac fluid (i.e., blood) during an operation by selectively cooling or warming the patient's cardiac fluid via a heat exchange unit 12. A first fluid circuit 13 circulates heat exchange fluid to and from the heat exchange unit 12. The heat exchange unit 12 includes a first chamber 14 and a second chamber 16. The first chamber 14 and second chamber 16 are isolated chambers such that respective fluids circulating within each of the respective chambers do not mix. A thermally conductive barrier 18 is disposed between the first chamber 14 and the second chamber 16 for allowing the temperature of fluid in the first chamber 14 to regulate the temperature of the fluid within the second chamber 16. A second fluid circuit 19 circulates the cardiac fluid of a patient 11 between the second chamber 16 of the heat exchange unit 12 and the patient 11 for allowing the temperature of the cardiac fluid to be regulated during surgery.

The system 10 includes a source of cooling such as a cold storage tank 20. The cold storage tank 20 typically includes an ice bath for cooling a heat exchange fluid (e.g., water) as it circulates through a heat exchange area in the cold storage tank 20.

The system 10 also includes a source of warming such as manifold unit 21. The manifold unit 21 includes a heating device 22 such as a resistive heating element for selectively warming the heat exchange fluid as it passes through the manifold unit 21. The manifold unit 21 includes a first temperature sensor 23, such as a thermistor, for measuring the temperature of the heat exchange fluid as it circulates through the manifold unit 21. The manifold unit 21 may also include a second temperature sensor 24 that is used as a fail-safe sensor for monitoring the temperature of the heat exchange fluid so that the temperature does not rise beyond a predetermined maximum limit. Precautionary measures may be taken if the temperature reaches the maximum limit.

A pump 26 is also provided within the first fluid circuit 13 for maintaining a predetermined flow rate of the heat exchange fluid to and from the heat exchange unit 12. The pump 26 is preferably disposed between manifold unit 21 and the heat exchange unit 12.

A rotary valve unit 28 is a multi-port valve to assist in regulating the temperature of heat exchange fluid to the heat exchange unit 12. The rotary valve unit 28 includes first inlet port 30, a first outlet port 32, a second inlet port 34, and a second outlet port 36 for receiving and outputting fluids to the respective components of the system 10. The first inlet port 30 of the rotary valve unit 28 is in fluid communication with the cold storage tank 20 via a first fluid channel 38 for receiving cooled heat exchange fluid from the cold storage tank 20. The first outlet port 32 of the rotary valve unit 28 is in fluid communication with manifold unit 21 via a second fluid channel 40. The second inlet port 34 is in fluid communication with the outlet of the first chamber 14 of the heat exchange unit 12 via a third fluid channel 42 for returning heat exchange fluid from the heat exchange unit 12 to the rotary valve unit 28. The second outlet port 36 is in fluid communication with the cold storage tank 20 via the fourth fluid channel 46 for returning heat exchange fluid received from the second inlet port 34 to the cold storage tank 20.

The pump 26 is fluidically coupled between manifold unit 21 and heat exchange unit 12. The pump 26 is preferably a centrifugal pump for pulling fluid from the rotary valve unit 28 for maintaining a constant fluid flow through the first circuit 13. Alternatively, the pump 26 may include other types of pumps such as axial, turbine, propeller, or reciprocating pumps.

Figure 2:
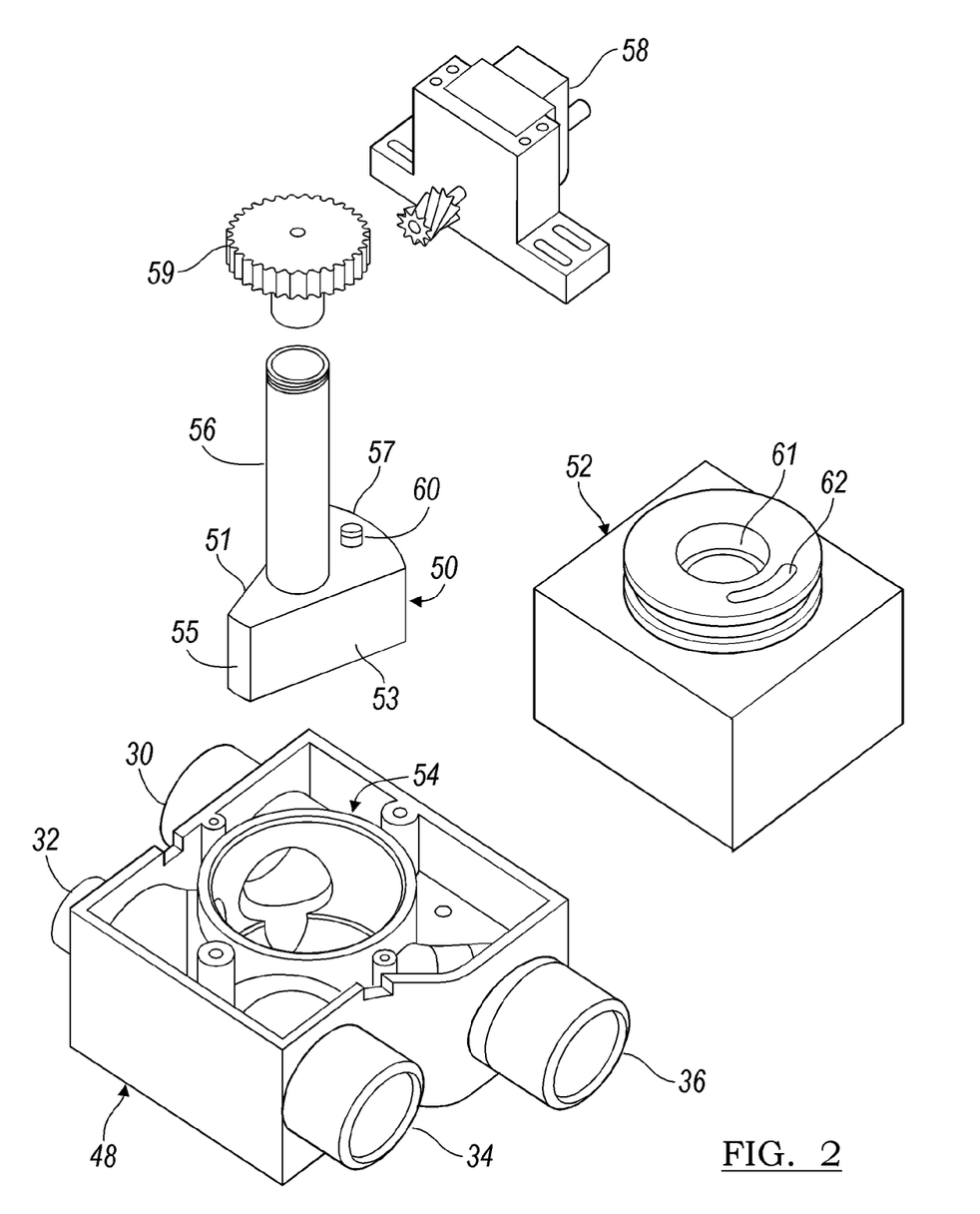
FIG. 2 illustrates an exploded view of the rotary valve unit according to a first preferred embodiment of the present invention.

FIG. 2 illustrates an exploded view of the rotary valve unit 28. The rotary valve unit 28 includes a valve body 48, a valve 50, and a valve cover 52. The components of the rotary valve unit 28 may be formed from a single type of material or various materials. For example, the valve body 48 may be formed from stainless steel, the valve 50 formed from a plastic such as CPVC, and the valve cover 52 formed from a plastic such as PVC. The valve body 48 includes the first inlet port 30, the first outlet port 32, the second inlet port 34, and the second outlet port 36. The valve body 48 further includes a valve chamber 54 centrally formed within the valve body 48. The valve chamber 54 is in fluid communication each of the respective ports 30, 32, 34, and 36.

The valve 50 is preferably a wedge-shaped member that is disposed within the valve chamber 54. The valve 50 includes first planar surface 51 and a second planar surface 53. The first planar surface 51 and the second planar surface 53 taper inward with respect to one another to form an adjoining and narrowed first end surface 55. The first planar surface 51 and the second planar surface 53 taper outward to a second end surface 57. The second end surface 57 is a wide arc-shaped end surface. The first end surface 55 and the second end surface 57 adjoin respective inner wall surfaces of the valve chamber 54 for selectively opening and closing the respective ports of the valve body 48.

The valve 50 rotates within the valve chamber 54 for controlling the blending of heat exchange fluid entering the valve chamber 54 from the first inlet port 30 and the return fluid from the second inlet port 34 for regulating a desired temperature of the heat exchange fluid output through the first output port 32. The valve 50 is rotatable to provide temperature regulation using either a cool-down mode, a maintain/heat mode, or a partial cool-down mode.

In a cooling mode, only the cooled heat exchange fluid received from the cold storage tank 20 is provided to the first outlet port 32. In a maintain/heat mode, only return heat exchange fluid directly from the heat exchange unit 12 is provided to the first outlet port 32. In a partial cool-down mode, a blending of exchange fluid from both the first inlet port 30 (i.e., from the cold storage tank 20) and the second inlet port 34 (i.e., directly from the heat exchange unit 12) is provided to the first outlet port 32.

Preferably, the respective ports are positioned asymmetric about the valve chamber 54. The asymmetric positioning of the respective ports 30, 32, 34, and 36, cooperate with the wedge-shaped valve for cooperatively providing a constant fluid flow through the first fluid circuit 13 (shown in FIG. 1) regardless of the position of the valve 50. The wedge-shaped design of the valve 50 also minimizes the overlapping areas between the walls of the valve 50 and the walls of the valve chamber 54. This provides an advantage of minimizing friction produced by any foreign particulates (e.g., scale) suspended in the heat exchange fluid that may come into contact between a respective wall of the valve 50 and a respective wall of the valve chamber 54.

The valve 50 is coupled to valve stem 56. The valve stem 56 may be a separately formed component from the valve 50 and fastened thereto, or may be integrally formed with the valve 50. The valve stem 56 extends through an aperture in the valve cover 52 for coupling to an external driving device 58 such as a stepper motor for rotating the valve 50. An intermediary coupling member 59 such as an intermediary gear may be used to couple a stepper motor 58 to the valve stem 56. Stepper motor 58 drives valve stem 56 to a position determined by a controller (not shown) of the heater/cool device.

The valve 50 may include a travel limit pin 60 for limiting the rotational travel of the valve 50 as it is rotated within the valve chamber 54. Preferably, the travel limit pin 60 is made of metal for durability purposes. Alternatively, the travel limit pin 60 may be made of other metals, alloys, or plastics.

The valve cover 52 includes a seal 61 for sealing the region between the valve stem 56 and the valve cover 52. The valve cover 52 further includes an arc-shaped slot 62 for receiving the travel limit pin 60. The travel limit pin 60 is limited in its rotational travel by the length of the arc-shaped slot 62.

Figure 3:
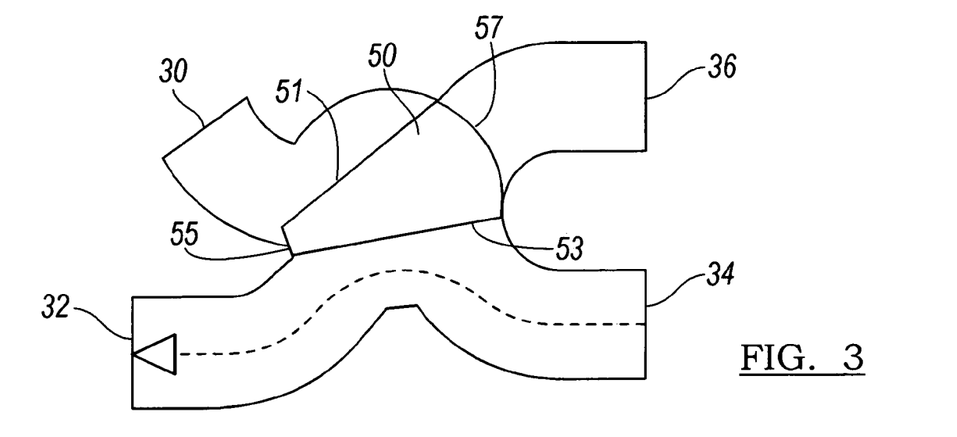
FIG. 3 illustrates a cross section view of the rotary valve unit in a non cool-down mode according to a first preferred embodiment of the present invention.

FIG. 3 illustrates a cross section view of the rotary valve unit 28 in a re-warm mode. In the re-warm mode, the valve 50 is positioned so that fluid flow within the valve chamber 54 between the first inlet port 30 and the second outlet port 36 is blocked. The first end surface 55 adjoins a respective inner wall surface of the valve chamber 54 between the first inlet port 30 and the first outlet port 32 whereas the second end surface 57 obstructs the entire opening of the second outlet port 36. In addition, the first planar surface 51 obstructs the entire opening of the first inlet port 30. As a result, cooled heat exchange fluid is prevented from circulating from the cold storage tank 20 to the first outlet port 32. The second planar surface 53 diverts the fluid entering the valve 50 from the second inlet port 34 to the first outlet port 32.

Referring to both FIG. 1 in general in cooperation with FIG. 3 to illustrate the operation of the valve 50, the second inlet port 34 and the first outlet port 32 remain open to allow heat exchange fluid to flow through the valve chamber 54 from the second inlet port 34 to the first outlet port 32. As a result, the heat exchange fluid within the system 10 (shown in FIG. 1) flows from the first outlet port 32 to the manifold unit 21 where the heat exchange fluid is warmed by the heating device if required. Depending on the desired temperature setting, the heating device may be active or inactive depending upon the sensed temperature of the heat exchange fluid. The pump 26 pulls the heat exchange fluid from the manifold unit 21 and generates a fluid flow to the heat exchange unit 12 where the cardiac fluid within the second chamber 16 is warmed by the heat exchange fluid circulating through the first chamber 14. The heat exchange fluid exits heat exchange unit 12 and is returned to the second inlet port 34 of the rotary valve unit 28. The heat exchange fluid continues in the re-warm circulation path until the valve 50 is rotated to a different position.

Figure 4:
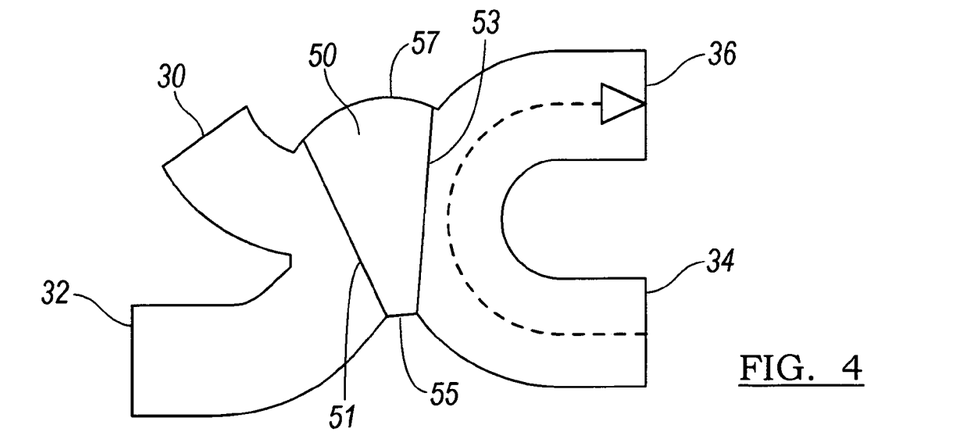
FIG. 4 illustrates a cross section view of the rotary valve unit in a cool-down mode according to a first preferred embodiment of the present invention.

FIG. 4 illustrates a cross section view of the rotary valve unit 28 in a cool-down mode. In the cool-down mode, the first end surface 55 is positioned to adjoin a respective inner wall surface of the valve chamber 54 between the first outlet port 32 and the second inlet port 34. The second end surface 57 is positioned to adjoin a respective inner wall surface of the valve chamber 54 between the first inlet port 30 and the second outlet port 36. The valve 50 is positioned so that neither the first end surface 55 nor the second end surface 57 block any of the respective ports; rather flow to and from the respective ports are selectively diverted by the first planar surface 51 and the second planar surface 53. As a result, the valve 50 is positioned so that heat exchange fluid flows from the second inlet port 34 to the second outlet port 36. In addition, heat exchange fluid flows from the first inlet port 30 to the first outlet port 32. All fluid flowing through the valve chamber 54 to the heat exchange unit 12 is redirected through the cold storage tank 20 for full cooling effects.

Referring to both FIG. 1 in general in cooperation with FIG. 4 to illustrate the operation of the valve 50, the valve 50 is positioned for directing all returning heat exchange fluid through the cold storage tank 20. Heat exchange fluid enters the second inlet port 34 and flows through the valve chamber 54 to the second outlet port 36. The position of the valve 50, as shown in FIG. 4, prevents heat exchange fluid flow directly to the first outlet port 32 from the second inlet port 34. The heat exchange fluid exits the second outlet port 36 and circulates through the cold storage tank 20. The cooled heat exchange fluid enters the valve chamber 54 via the first inlet port 30 and exits via the first outlet port 32. Cooled heat exchange fluid is pulled through the manifold unit 21 by the pump 26 and generates a fluid flow to the heat exchange unit 12 where the cardiac fluid within the second chamber 16 is cooled by the heat exchange fluid circulating through the first chamber 14. The heat exchange fluid exits the heat exchange unit 12 and is returned to the second inlet port 34 of the rotary valve unit 28. The heat exchange fluid continues in the cool-down circulation path until the valve 50 is rotated to a different position.

Figure 5:
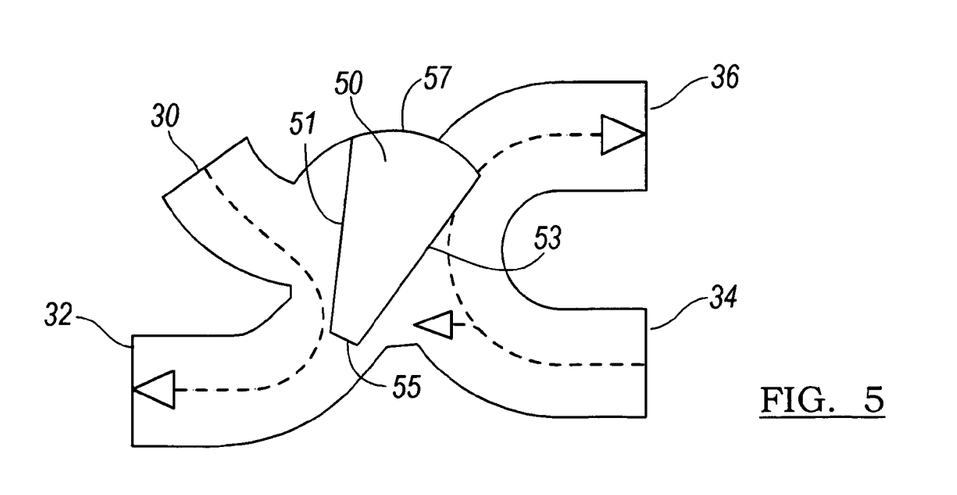
FIG. 5 illustrates a cross section view of the rotary valve unit in a partial cool-down mode according to a first preferred embodiment of the present invention.

FIG. 5 illustrates a cross section view of the rotary valve unit 28 in a partial cool-down mode. Referring to FIG. 1 in general in cooperation with FIG. 5 to illustrate the position of the valve 50, the partial cool-down mode is now described. In the partial cool-down mode, a lesser magnitude of cooling is demanded by the system 10 than that which cool-down mode provides. Therefore, the heat exchange fluid from cold storage tank 20 is blended with returning heat exchange fluid that by-pass the cold storage tank 20 to achieve the desired temperature setting in partial-cool down mode.

In the partial cool-down mode, the first end surface 55 is positioned within the opening of the first outlet port 32 and contacts no inner wall surface of the valve chamber 54. This allows fluid flow from both the first inlet port 30 and second inlet port 34 to the first outlet port 32. A first portion of the second end surface 57 is positioned to adjoin a respective inner wall surface between the first inlet port 30 and the second outlet port 36 while a second portion of the second end surface 57 partially obstructs the second outlet port 36. As a result, the valve 50 is positioned such that both a portion of the heat exchange fluid received from the cold storage tank 20 and a portion of the heat exchange fluid received directly from the heat exchange unit 12 are provided to the heat exchange device 12. The returning heat exchange fluid from the heat exchange unit 12 enters the second inlet port 34. The positioning of the valve 50 allows returning heat exchange fluid to be diverted directly to both the second outlet port 36 and the first outlet port 32. The returning heat exchange fluid directed to the second outlet port 36 is circulated through the cold storage tank 20 where the fluid is cooled down. The cooled heat exchange fluid exiting the cold storage tank 20 enters the rotary valve unit 28 via the first inlet port 30. The positioning of the valve 50 diverts the cooled heat exchange fluid to the first outlet port 32. A portion of the returning heat exchange fluid entering the second inlet port 34 is also diverted to the first outlet port 32 where the cool-down heat exchange fluid is blended with the returning heat exchange fluid for providing a heat exchange fluid to the heat exchange unit 12 having a temperature between the temperature of the cool-down fluid exiting the cold storage tank 20 and the returning the heat exchange fluid from the heat exchange unit 12.

As the blended heat exchange fluid is circulated to the manifold unit 21, the temperature of the blended heat exchange fluid is measured. Further adjustments to the temperature of the heat exchange unit 12 may be made by positioning the valve 50 to allow for greater fluid flow or less fluid flow from the cold storage tank 20. As discussed earlier, the manifold unit 21 may include a second temperature sensor to be used as a safety temperature sensor. The safety temperature sensor is used as a secondary backup sensor to monitor the temperature of the heat exchange fluid provided to the heat exchange unit 12 so that the temperature of the fluid does not extend beyond a predetermined maximum limit.

Figure 6:
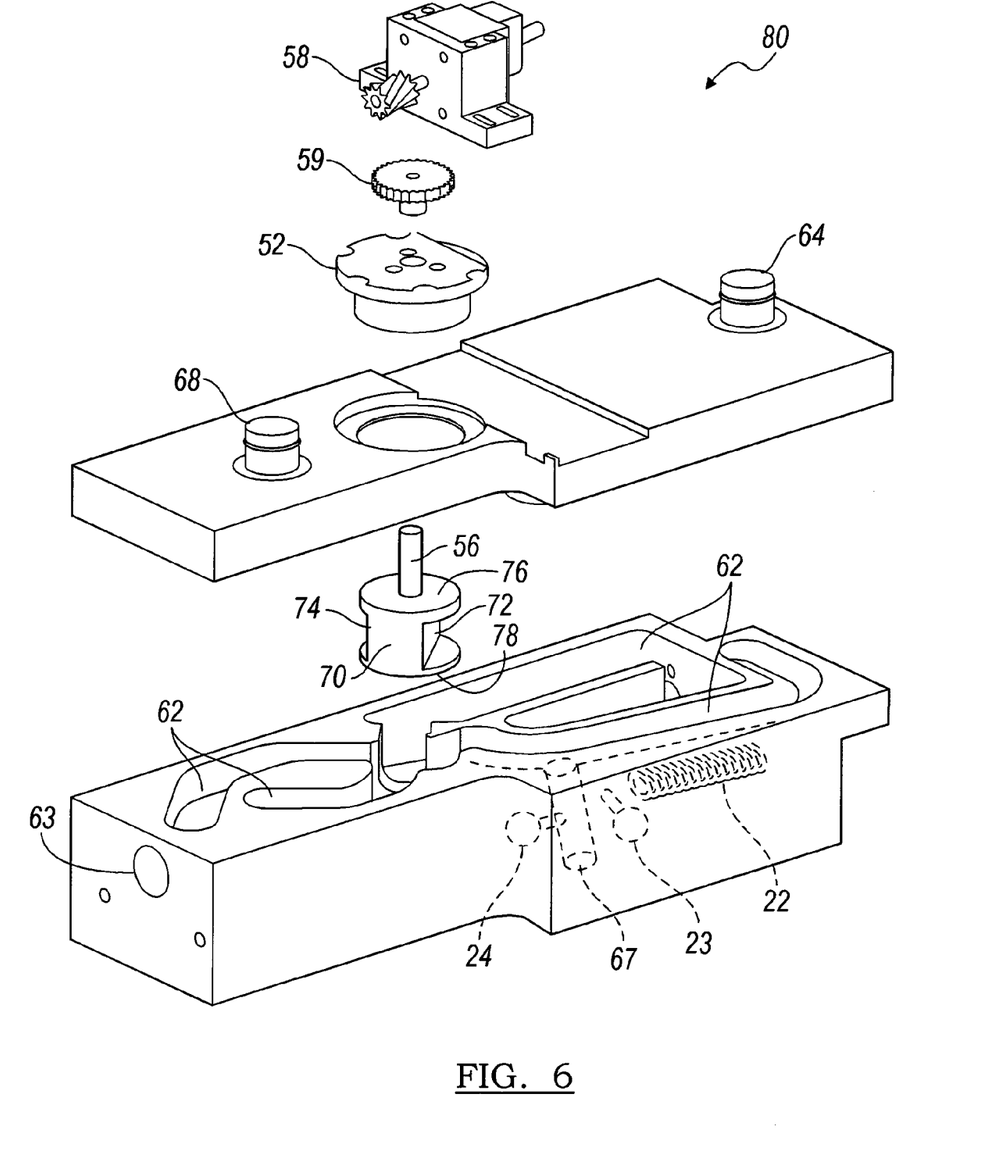
FIG. 6 illustrates an exploded view of a manifold module according to a second preferred embodiment of the present invention.

FIG. 6 illustrates an alternative manifold 80 according to a second preferred embodiment. The manifold module 80 integrates the manifold unit and a valve 70 into a single module. The manifold module 80 includes a plurality of fluid channels 62 formed in the manifold module 80 that extend to the respective inlet ports 63, 64 and respective outlet ports 67, 68. A valve 70 is disposed at the intersection of the plurality of fluid channels 62. The valve 70 is cylindrical-shaped similar to a spool. Planar surfaces 72 and 74 are formed in a circumferential body portion of the valve 70 for forming a wedge-shaped body. Cylindrical disks 76 and 78 are formed on the axial end portions of the valve 70. The valve stem 56 is coupled to or formed integral with the valve 70. The valve stem 56 extends to an exterior of the manifold module 80 for being operationally coupled to a driving device 58 such as a stepper motor. The plurality of channels 62 and respective ports in cooperation with the valve 70 function in a substantially similar manner as the rotary valve unit 28 discussed in FIGS. 1-5. The heating device 22 is positioned proximal to the respective fluid channel leading to the outlet port 67 so that the fluid flowing to the heat exchange unit 12 (shown in FIG. 1) may be warmed, if required. The manifold module 80 may be made of a uniform material such as Delrin. Alternatively, other materials may be used. Temperature sensors 23 and 24 are integrated within the manifold module 80 proximal to the respective fluid channel leading to the outlet port 67 to monitor the temperature of the fluid. The temperature sensors 23 and 24 function in the same manner as discussed earlier. The integration of the valve 70 and the manifold unit into a single module allows the manifold module 80 to be easily incorporated into the extracorporeal blood perfusion system with less hydraulic fluid connections.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A rotary valve unit for blending hot and cold fluid sources to regulate a temperature of fluid flowing to a heat exchange unit in an extracorporeal blood perfusion circuit comprising:

a valve body comprising:

a valve chamber including a first inlet port, a second inlet port, a first outlet port, and a second outlet port;

a first fluid channel in fluid communication with the first inlet port, the first fluid channel receiving a cold fluid from a cold storage tank;

a second fluid channel in communication with the first outlet port, the first outlet port returning fluids received from at least one of the inlets ports to the heat exchange unit;

a third fluid channel in fluid communication with the second inlet port, the third fluid channel receiving a returned fluid from the heat exchange unit;

a fourth fluid channel in communication with the second outlet port, the fourth fluid channel returning fluids received from the second inlet port to the cold storage tank; and a wedge-shaped rotary valve disposed within the valve chamber, the rotary valve being rotatable within the valve chamber for controlling a blending of the cold fluid entering the valve chamber from the first inlet port and the return fluid from the heat exchange unit entering the valve chamber from the second inlet port to regulate the desired temperature of fluid provided to the heat exchange unit, the wedge-shaped rotary valve being positionable to provide either only the cold fluid to the first outlet port, only the return fluid to the first outlet port, or a blending of the cold fluid and return fluid to the first outlet port.

2. The rotary valve unit of claim 1 further comprising a valve cover for sealing the wedge-shaped rotary valve with the valve chamber.

3. The rotary valve unit of claim 1 wherein the wedge-shaped rotary valve includes a travel limit pin for limiting a rotational travel of the wedge-shaped rotary valve within the valve chamber.

4. The rotary valve unit of claim 3 wherein the travel limit pin is metal.

5. The rotary valve unit of claim 1 wherein the wedge-shaped rotary valve is coupled to a valve stem, the valve stem being adapted to be coupled to a motor for rotating the wedge-shaped rotary valve.

6. The rotary valve unit of claim 5 wherein the valve stem is plastic.

7. The rotary valve unit of claim 6 wherein the valve stem further comprises a metal shaft centrally secured within the plastic valve stem, the metal shaft being adapted to be coupled to the motor.

8. The rotary valve unit of claim 1 wherein the wedge-shaped rotary valve is made of plastic.

9. An extracorporeal blood temperature management system for controlling the temperature of cardiac fluids in an extracorporal blood perfusion circuit during surgery, the system comprising:

a heat exchange unit;

a multi-port valve body including a valve chamber, the valve chamber including a first inlet port, a second inlet port, a first outlet port, and a second outlet port;

a rotary valve disposed within the valve chamber, the rotary valve being rotatable within the valve chamber for fluidically coupling at least two ports of the valve chamber;

a first fluid circuit coupled to the multi-port valve body for distributing the heat exchange fluid to a heat exchange unit;

a cold storage tank coupled to the first fluid circuit between the first inlet port and the second outlet port for cooling the heat exchange unit;

a manifold unit coupled to the first fluid circuit between the first outlet port and the heat exchange unit, the manifold unit including a heating element for heating the heat exchange fluid;

a pump for maintaining a fluid flow of heat exchange fluid to the heat exchange unit within the first fluid circuit;

a second fluid circuit for distributing cardiac fluid to the heat exchange unit; and a controller for controlling the rotation of the rotary valve for regulating the temperature of the heat exchange fluid within the first fluid circuit that is provided to the heat exchange unit, the heat exchange fluid within the first fluid circuit provided to the heat exchange unit regulates the cardiac fluid of the second fluid circuit that that is provided to the heat exchange unit.

10. The extracorporeal blood temperature management system of claim 9 wherein the manifold unit includes a temperature sensor for sensing the temperature of the heat exchange fluid provided to the heat exchange unit.

11. The extracorporeal blood temperature management system of claim 9 wherein the manifold unit includes a second temperature sensor for sensing a predetermined maximum temperature limit.

12. The extracorporeal blood temperature management system of claim 9 further comprising a motor coupled to the rotary valve for rotationally driving the rotary valve for blending cold fluid from the cold storage tank and the return fluid from the heat exchange unit.

13. The extracorporeal blood temperature management system of claim 12 wherein the motor includes a stepper motor.

14. The extracorporeal blood temperature management system of claim 12 wherein the rotary valve includes a valve stem for coupling to the motor.

15. The extracorporeal blood temperature management system of claim 9 wherein the first inlet port, second inlet port, first outlet port, and second outlet port are spaced asymmetrical about the valve chamber.

16. The extracorporeal blood temperature management system of claim 9 wherein the pump includes a centrifugal pump.

17. The extracorporeal blood temperature management system of claim 1 wherein the pump is fluidically coupled between the manifold and that heat exchange unit.

18. A manifold module for blending hot and cold fluid sources to regulate a temperature of fluid flowing to a heat exchange unit in an extracorporeal blood perfusion circuit comprising:

a valve body comprising:
a valve chamber including a first inlet port, a second inlet port, a first outlet port, and a second outlet port;

a first fluid channel in fluid communication with the valve chamber via a first inlet port, the first fluid channel receiving a cold fluid from a cold storage tank;

a second fluid channel in fluid communication with the valve chamber via the first outlet port, the second fluid channel returning fluid to the heat exchange unit;

a third fluid channel in communication with the valve chamber via the second inlet port, the third fluid channel returning fluids received from the heat exchange unit to the second inlet port;

a fourth fluid channel in communication with the valve chamber via the second outlet port, the second outlet port returning fluids received from the second inlet port to the cold storage tank;

a wedge-shaped rotary valve disposed within the valve chamber, the rotary valve being rotatable within the valve chamber for controlling a blending of the cold fluid entering the valve chamber from the first inlet port and the return fluid from the heat exchange unit entering the valve chamber from the second inlet port to regulate the desired temperature of fluid provided to the heat exchange unit, the wedge-shaped rotary valve being positionable to provide either only the cold fluid to the first outlet port, only the return fluid to the first outlet port, or a blending of the cold fluid and return fluid to the first outlet port;

a heating unit for warming heat exchange fluid exiting the first outlet port; and a temperature sensor for monitoring the temperature of the heat exchange fluid exiting the first outlet port.

19. The manifold module of claim 18 wherein the manifold unit includes a second temperature sensor for sensing a predetermined maximum temperature limit.

* * * * *